US012708610B2

(12) United States Patent
Russi

(10) Patent No.: US 12,708,610 B2
(45) **Date of Patent: *Aug. 18, 2026**

(54) PROTECTION OF POLYUNSATURATED FATTY ACIDS FROM RUMINAL DEGRADATION

(71) Applicant: One Idea LLC, Merced, CA (US)

(72) Inventor: Juan Pablo Russi, Buenos Aires (AR)

(73) Assignee: ONE IDEA LLC, Merced, CA (US)

( * ) Notice: Subject to any disclaimer, the term of this patent is extended or adjusted under 35 U.S.C. 154(b) by 805 days.

This patent is subject to a terminal disclaimer.

(21) Appl. No.: 18/048,215

(22) Filed: Oct. 20, 2022

(65) Prior Publication Data

US 2023/0137807 A1 May 4, 2023

Related U.S. Application Data

(60) Continuation-in-part of application No. 17/810,934, filed on Jul. 6, 2022, now Pat. No. 12,496,286, which (Continued)

(51) Int. Cl.
*A61K 31/202* (2006.01)
*A61K 9/00* (2006.01)

(Continued)

(52) U.S. Cl.
CPC .......... *A61K 31/202* (2013.01); *A61K 9/0056* (2013.01); *A61K 47/14* (2013.01); *A61K 47/26* (2013.01)

(58) Field of Classification Search
CPC .... A61K 31/202; A61K 9/0056; A61K 47/14; A61K 47/26; A61K 9/1272; A61K 9/1277
See application file for complete search history.

(56) References Cited

U.S. PATENT DOCUMENTS 3,595,678 A 7/1971 Shimazaki et al.
4,957,748 A 9/1990 Winowiski (Continued)

FOREIGN PATENT DOCUMENTS

CA 2099529 C 1/2002
WO 1996/041543 A1 12/1996

(Continued)

OTHER PUBLICATIONS

C. Benchaar et al., Journal of Dairy Science, vol. 90, Issue 2, 2007, pp. 886-897. (Year: 2007).*

(Continued)

*Primary Examiner* — Clinton A Brooks
*Assistant Examiner* — Izabela Schmidt
(74) *Attorney, Agent, or Firm* — FOX ROTHSCHILD LLP

(57) ABSTRACT

A method of preparing rumen-protected lipid-soluble nutritional supplements for use in ruminant feeds by inducing the Maillard reaction between a reducing carbohydrate source and de-oiled lecithin in the presence of a lipid-soluble fraction containing one or more lipid-soluble nutritional supplement compounds under reduced pressure conditions. Lipid-soluble nutritional supplement compounds may include lipid-soluble nutraceuticals such as essential oils. The lipid-soluble fraction may further include Polyunsaturated Fatty Acids (PUFAs). Products made by the process, as well as methods for enhancing performance, assisting the induction of pregnancy, alleviating inflammation, modulating fetus growth, improving immune system function, and modulation of the fatty acid composition of meat and milk of ruminant animals are also disclosed.

13 Claims, 6 Drawing Sheets

Related U.S. Application Data is a division of application No. 16/722,358, filed on Dec. 20, 2019, now Pat. No. 11,389,418.

(60) Provisional application No. 62/782,619, filed on Dec. 20, 2018.

(51) Int. Cl.
*A61K 47/14* (2017.01)
*A61K 47/26* (2006.01)

(56) References Cited

U.S. PATENT DOCUMENTS

| | | | |
|---|---|---|---|
| 5,023,091 A | 6/1991 | Winowiski | |
| 5,064,665 A | 11/1991 | Klopfenstein et al. | |
| 5,789,001 A | 8/1998 | Klopfenstein et al. | |
| 6,221,380 B1 | 4/2001 | Woodroofe et al. | |
| 6,322,827 B1 | 11/2001 | Scott et al. | |
| 6,506,423 B2 | 1/2003 | Drouillard et al. | |
| 7,303,775 B1 | 12/2007 | Patton et al. | |
| 8,507,025 B2 | 8/2013 | Russi | |
| 11,389,418 B2 * | 7/2022 | Russi | A23K 50/10 |
| 2006/0039955 A1 | 2/2006 | Messman et al. | |
| 2007/0009502 A1 | 1/2007 | Lall et al. | |
| 2007/0232647 A1 | 10/2007 | Goetze et al. | |
| 2009/0196949 A1 | 8/2009 | Winowiski | |
| 2011/0064860 A1 * | 3/2011 | Lamb | A23J 7/00 426/656 |
| 2011/0195146 A1 * | 8/2011 | Russi | A23K 20/163 426/89 |
| 2016/0174595 A1 | 6/2016 | Miller et al. | |
| 2018/0070611 A1 | 3/2018 | Wan et al. | |

FOREIGN PATENT DOCUMENTS

| | | | |
|---|---|---|---|
| WO | WO-9641543 A1 * | 12/1996 | A23K 50/10 |
| WO | 2005025323 A1 | 3/2005 | |

OTHER PUBLICATIONS

Bell, A. W. "Regulation of organic nutrient metabolism during transition from late pregnancy to early lactation". J Anim Sci 73: 2804-2819. (1999).

Berg & Schmidt., "BergaLac: The New Rumenstable Energy Supplier for Early Laction," Nov. 2006 [retrieved Feb. 12, 2020] retrieved from internet url: <https://www.berg-schmidt.de/pdf/newsletter_2_2006_E.pdf>.

Drackley, J. K. "Biology of Dairy Cows During the Transition Period: the Final Frontier?" Journal of Dairy Science 82(11):2259-2273. (1999).

Drackley, et al. "Adaptations of Glucose and Long-Chain Fatty Acid Metabolism .cndot. in Liver of Dairy Cows During the Periparturient Period". Journal of Dairy Science 84(E. Suppl.):E100-E112. (2001).

Oginni et al., "Effect of starch gelatinization and vacuum frying conditions on structure development and associated quality attributes of cassava-gluten based snack," Food Structure (2015): 3:12-20.

Wheelock, et al. "Effects of heat stress on energetic metabolism in lactating Holstein cows". Journal of Dairy Science 93(2): 644-655. (2010).

Drackley, et al. "Adaptations of Glucose and Long-Chain Fatty Acid Metabolism in Liver of Dairy Cows During the Periparturient Period". Journal of Dairy Science 84(E. Suppl.):E100-E112. (2001).

Francisquini, et al., "Maillard Reaction: A Review" Cândido Tostes Dairy Institute Magazine, Jan. 2017, vol. 72, No. 1, pp. 48-57.

* cited by examiner

10 - Soybean Lecithin

20 - Reducing Sugar

30 - Polyunsaturated fatty acids

PROTECTION OF POLYUNSATURATED FATTY ACIDS FROM RUMINAL DEGRADATION

CROSS-REFERENCE TO RELATED APPLICATIONS

This application is a continuation-in-part of the U.S. application Ser. No. 17/810,934 filed Jul. 6, 2022, which is a divisional application of U.S. application Ser. No. 16/722,358 filed Dec. 20, 2019, which is patented as U.S. Pat. No. 11,389,418 issued Jul. 19, 2022, and claims the benefit of priority of U.S. Provisional Application No. 62/782,619, filed on Dec. 20, 2018, the disclosure of which is incorporated herein by reference in its entirety.

FIELD OF THE INVENTION

The present invention relates to providing a source of rumen-protected polyunsaturated fatty acid (RuPUFA) particularly docosahexaenoic acid (DHA) to the small intestine, for example fed during lactation to alter the fatty acid profile in milk or during the finishing phase in beef animals to alter the fatty acid profile of meat; also during the transition from late gestation to early lactation period in dairy cows to cope with stress, lower inflammation and improve the pregnancy rate, as well as during the last part of pregnancy to influence the offspring's performance and future milk yield capacity. Also, for example, fed during the whole lactation to help maintain the integrity of the intestinal barrier and its function.

BACKGROUND

Feeding polyunsaturated fatty acids in ruminant diets has been explored for many years in order to obtain milk and beef products with better nutritional characteristics, altering its fatty acid profiles.

Specifically, DHA is a polyunsaturated fatty acid that has benefits beyond changing or modulating the fatty acid profile of ruminant's end products. Fed during the transition from late gestation to early lactation period, DHA will help to cope with stress and inflammation, helping the cow to start its reproductive cycle again, when fed during the last trimester of gestation it will enhance progeny productive performance, which is known as fetal programming in a ruminant. When fed to cows during period of stress where the intestinal barrier is more permeable it will help with its integrity and repair and its well being.

Feeding polyunsaturated fatty acids (PUFA) or other fats or nutraceuticals or medicaments to ruminants is not straightforward. First, there is a limit on the inclusion rate in order to sustain a normal fermentation in the rumen. Second, when PUFAs are fed to ruminants, the polyunsaturated fatty acids are biohydrogenated to a large extent and transformed into more saturated intermediates fatty acids, some of which might upset production, lowering milk fat % and total milk production. The same happens with nutraceuticals and medicaments which will be altered by the rumen microbes and reach the intestine usually having lost its desired effect.

U.S. Pat. No. 2005/0171367 A1 discloses the use of lecithin as part of the formula to react and make calcium soaps with other fatty acids in a saponification process, but without first removing the oil from the lecithin by solvent extraction.

US Patents No. 2005/0255145A1 and 2010/023106A1 disclose the use of lecithin as a coating agent simply by drying it over the product to be protected, for example, an animal feed like soybean meal (2005/0255145A1), or aminoacids, vitamins or medications (2010/023106A1). The lecithin is not reported to have been de-oiled.

U.S. Pat. Nos. 4,957,748, 5,789,001 and 6,221,380 disclose the use of Maillard reaction products, but only as a method to produce rumen-inert lipids and proteins without mentioning lecithin or a specific Maillard reaction between the amino groups in lecithin and any reducing carbohydrate to obtain the ruminal protection.

U.S. Pat. No. 8,507,025 discloses an energy supplement for ruminant animals prepared by a Maillard reaction method conducted under positive pressure (1 to 2 atmospheres) without using lecithin as a raw material and with the objective of feeding an energy supplement with glucose as a main nutrient to the animals.

There remains a need for a product that includes a source of rumen-protected polyunsaturated fatty acids (RuPUFA) that will help change the fatty acid profile of milk and meat, help the transition cows cope with stress and accelerate pregnancy, and function as an enhancer on the offspring of the animals when fed during the last trimester of lactation. When fed during the whole lactation period, RuPUFAs can help to maintain the intestinal barrier integrity and its function.

All of the patents above mentioned as an industrial process use atmospheric pressure to manufacture the final product.

SUMMARY OF THE DISCLOSURE

The present invention is directed to the preparation of rumen-protected polyunsaturated fatty acids (RuPUFAs), such as docosahexaenoic acid (DHA), using a reduced pressure Maillard reaction between the amino groups in lecithin (phosphatidylcholine and phosphatidylethanolamide, where the lecithin has been de-oiled by solvent extraction pretreatment to remove the oil) and a reducing carbohydrate, in order to coat and protect the polyunsaturated fatty acid from ruminal degradation. The invention is also directed to the rumen-protection of other lipid soluble nutritional supplements, with or without PUFAs. The present invention makes DHA or any unsaturated fatty acid or unsaturated fatty acid combination available to the ruminant animal as a rumen-bypass nutrient. The invention also makes any lipid-soluble nutrient compound available to ruminant animals as rumen-bypass nutrients. This product could be used to enhance performance, assist in induction of pregnancy, alleviate inflammation, modulate fetus growth, improve immune system function, and modulate the fatty acid composition of the animal's tissues and milk.

For an industrially robust process, it has now been unexpectedly discovered that for the preparation of the Maillard reaction product between lecithin's amino groups and a reducing carbohydrate can be conducted by heating under less than atmospheric pressure, i.e. under a vacuum, and where the lecithin has had any oil removed by solvent extraction pretreatment.

The present invention includes methods according to which the product of the present invention is made, as well as products made by the inventive method. As known in the art, when certain foods are heat-treated under moist conditions Maillard-type reactions can occur. These reactions initially involve a condensation between the carbonyl group of a reducing sugar with the free amino group of an amino acid, protein, urea or other suitable nitrogen source, such as the phosphatidylcholine and phosphatidylethanolamide present in lecithin extracted from soybean oil refining. The result is a Maillard reaction product. For this Maillard reaction to proceed efficiently, the lecithin must be purified by pretreatment to remove residual oil, preferably by solvent extraction. The present invention incorporates the discovery that the Maillard reaction, specifically a Maillard reaction conducted at reduced pressure (below atmospheric pressure) under specific reaction conditions, can be advantageously employed to create rumen-protected lipid-soluble nutritional supplement compounds, with or without fatty acids (RuPUFAs), that can be used as a ruminant nutritional supplement.

The structure of the RuPUFAs is shown in FIG. 1. The PUFA, 30, is encapsulated within the Maillard reaction product of lecithin, 10, and reducing sugar, 20.

As disclosed herein, a method of preparing lipid-soluble nutritional supplement compounds protected from ruminal degradation comprises:

- mixing a reducing carbohydrate source, de-oiled lecithin and a lipid-soluble fraction containing one or more lipid-soluble nutritional supplement compounds where the amount by weight of the reducing carbohydrate source is less than the amount of lecithin and the lipid-soluble fraction, to provide a mixture; and
- heating and mixing the mixture for about 7 min to about 240 min, at a temperature between about 30° C. and about 135° C., and pressure between about 0.4 Atm and about 0.9 Atm, in the presence of sufficient moisture so that a Maillard reaction product is formed and the lipid-soluble nutritional supplement compounds and lecithin are not degraded, where the amount of lecithin and the heating time, temperature, reduced pressure and moisture conditions are sufficient to provide an amount of a Maillard reaction product effective to prevent ruminal biohydrogenation of the lipid soluble nutritional supplement compounds.

Lipid-soluble nutritional supplement compounds suitable for use in the present invention include lipid-soluble nutraceutical compounds, lipid soluble prebiotics probiotics, and lipid soluble medicaments as well as lipid soluble vitamins that provide health or nutritional benefits to ruminants. The method adds one or more lipid-soluble nutraceuticals lipid soluble prebiotics probiotics, and lipid soluble medicaments as well as lipid soluble vitamins to the Maillard reaction mixture. Alternatively, one or more of lipid-soluble nutraceuticals lipid soluble prebiotics probiotics, and lipid soluble medicaments as well as lipid soluble vitamins can be added to the Maillard reaction product after the heating process.

The nitrogen source for the Maillard reaction resides in the phosphatidylcholine and phosphatidylethanolamide present in lecithin, or any other N group in lecithin. The lecithin should be de-oiled and purified to a purity of at least 95% by pretreatment to remove the oil, preferably using solvent extraction.

When added to the reaction mixture, polyunsaturated fats can include C18, C20 or C22 fatty acids or derivatives thereof, preferably docosahexaenoic acid (DHA; 22:6,n-3) and eicosapentaenoic (EPA; 20:5,n-3) acid. Derivatives of the fatty acids can include esters.

Lipid-soluble nutraceutical compounds suitable for use in the present invention include other fats, fat-soluble vitamins, essential oils and/or other lipophilic nutrients, so that the Maillard reaction product includes other fats, fat-soluble vitamins, essential oils and/or other lipophilic nutrients. Essential oils suitable for use in the present invention include basil oil, carrot seed oil, celery seed oil, Citronella oil, coriander oil, garlic oil, grapefruit oil, lemon oil, marjoram oil, onion oil, organum oil, parsley oil, rosemary oil, sage oil, tarragon oil, thyme oil, cannabis oil, and any lipid-soluble plant extracts, each used alone or in combination. Lipid soluble probiotics can include *Lactobacillus* rhanmoses GG, *Lactobacillus reuteri*, bifidobacteria and certain strains of *Lactobacillus casei*, the *Lactobacillus acidophilus*-group, *Escherichia coli* strain Nissle 1917, *Enterococcus faecium* SF68, and the probiotic yeast *Saccharomyces boulardii*, or its fermentation end products that are beneficial to gastrointestinal function and well-being, and the fungi *Aspergillus* sp and their fermentation by products.

Lipid soluble prebiotics, although usually carbohydrates, can be blended into the lecithin and made non available for rumen microbes, like glucomannans from yeast cell wall, inulin, its hydrolysis product oligofructose, and (trans)galacto-oligosaccharides), or galacto-oligosaccharides.

Lipid soluble medicaments like, penicillin, ampicillin, ampicillin-sublactam, nafcillin, amoxicillin, cloxacillin, methicillin, oxacillin, dicloxacillin, azocillin, bacampicillin, ciclacillin, carbenicillin, carbenicillin indanyl, mezlocillin, penicillin G, penicillin V, ticarcillin, piperacillin, aztreonam, imipenem, cephalosporins, cephapirin, cefaxolin, cephalexin, cephradine, cefadroxil, cefamandole, cefoxitin, cefaclor, cefuroxime, cefuroxime axetil, cefonicid, cefotetan, ceforanide, cefotaxime, ceftizoxime, ceftriaxone, cefoperazone, ceftazidime, tetracyclines, demeclocycline tetracycline, doxycycline, methacycline, minocycline, oxytetracycline, beta-lactamase inhibitors, clavulanic acid, aminoglycosides, amikacin, gentamicin C, kanamycin A, neomycin B, netilmicin, streptomycin, tobramycin, erythromycin, clindamycin, spectinomycin, vancomycin, bacitracin, isoniazid, rifampin, ethambutol, aminosalicylic acid, pyrazinamide, ethionamide, cycloserine, dapsone, sulfoxone sodium, clofazimine, sulfonamides, sulfanilamide, sulfamethoxazole, sulfacetamide, sulfadiazine, sulfisoxazole, trimethoprim-sulfamethoxazole, quinolones, nalidixic acid, cinoxacin, norfloxacin, ciprofloxacin, methenamine, nitrofurantoin, phenazo-pyridine, chloroquine, emetine, dehydroemetine, 8-hydroxyquinolines, metronidazole, quinacrine, melarsoprol, nifurtimox, pentamidine, amphotericin-B, flucytosine, ketoconazole, miconazole, itraconazole, griseofulvin, clotrimazole, econazole, terconazole, butoconazole, ciclopirox olamine, haloprogin, tolnaftate, naftifine, nystatin, natamycin, undecylenic acid, benzoic acid, salicylic acid, propionic acid, caprylic acid, zidovudine, acyclovir, ganciclovir, vidarabine, idoxuridine, trifluridine, foxcarnet, amantadine, rimantadine, tee tree oil, ribavirin, metronidazole, mebendazole, albendazole, milbemycin, ivermectin, praziquantel, artemisinin, quinine, chloroquine, halofantrine, mefloquine, lumefantrine, amodiaquine, pyronaridine, piperaquine, primaquine, tafenoquine, atovaquone, artemether, artesunate, dihydroartemisinic, artemisinin, proguanil, tetracyclines, pentamidine, suramin, melarsoprol, amphotericin, eflorni-thine, benznidazole, aminosidine, nortriptyline, amitriptyline, lidocaine, capsaicin, gabapentin, pregabalin, carbamazepine, duloxetine, venlafaxine, oxycodone, tramadol, nitinol, or combi-nations thereof.

Lipid soluble vitamins like vitamin A, All-trans-Retinol (Retinal, Retinoic acid, Retinoids), carotenoids (alpha-carotene, beta-carotene, gamma-carotene) Xanthophyll beta-cryptoxanthin, vitamin K Menaquinone, Phylloquinone. vitamin E Tocopherols, tocotrienols; vitamin D sitocalciferol 22-dihydroergocalciferol, D3 cholecalciferol, ergocalciferol. The de-oiled lecithin can be further extracted with an alcohol to remove residual sugars.

The method can further include adding water to the mixture to give a moisture content of about 20% to 25% by weight.

The PUFA can include docosahexaenoic acid (DHA).

The PUFA can also include eicosapentaenoic acid (EPA).

The reducing carbohydrate source can be selected from fructose, sucrose which has been treated to yield glucose and fructose, dextrose, high fructose corn syrup, glucose, lactose, molasses, xylose, and spent sulfite liquor.

The reducing carbohydrate source can be dissolved in water before mixing with the combination of lecithin and the lipid-soluble fraction. The mixture can be pre-heated before cooking at reduced pressure, using conventional heated mixing equipment.

The mixture, with or without pre-heating, can be heated to a temperature between about 60° C. and about 90° C., or between about 60° C. and about 85° C., or between about 60° C. and about 80° C. The pressure during heating can be between about 0.4 Atm and about 0.9 Atm, or between about 0.4 Atm and about 0.6 Atm, or between about 0.4 Atm and about 0.5 Atm.

The mixture heating time can be about 0.5 min to about 240 min depending on the temperature and pressure used. Preferably, the reaction time is between about 30 seconds and about 4 hours. The mixture heating time can be about 45 min.

The weight ratio of reducing carbohydrate to lecithin can be about 5:95 to less than 50:50. The weight ratio of reducing carbohydrate to lecithin can be about 5:95. The weight ratio of reducing carbohydrate to lecithin can be about 10:90. The weight ratio of reducing carbohydrate to lecithin can be about 7:93. The weight ratio of reducing carbohydrate to lecithin can be less than 20:80. The weight ratio of reducing carbohydrate to lecithin can be less than 30:70. The weight ratio of reducing carbohydrate to lecithin can be less than 40:60. The weight ratio of reducing carbohydrate to lecithin can be less than 50:50. As disclosed herein, a polyunsaturated fatty acid (PUFA) supplement for use in ruminant animal feed comprises rumen-protected PUFA and can be prepared by the methods as described herein.

The invention is also directed to the rumen-protection of other lipid-soluble nutrients, with or without PUFAs.

The method of protecting lipid-soluble nutritional supplement compounds from rumen degradation includes the steps of:

- mixing de-oiled lecithin and a lipid-soluble fraction containing one or more lipid-soluble nutritional supplement compounds with water at a temperature of 25° C.;
- after obtaining a homogeneous mixture, adding the reducing carbohydrate in a quantity less than that of the de-oiled lecithin and the one or more lipid-soluble nutrients, and continue mixing until the mixture is homogeneous again; and
- heating the mixture for about 7 min to about 120 min, optionally up to 240 min, at a temperature between about 30° C. and about 135° C., and a pressure between about 0.4 Atm and about 0.9 Atm, in the presence of sufficient moisture so that a Maillard reaction product is formed in an amount sufficient to prevent ruminal biohydrogenation of the one or more lipid-soluble nutritional supplement compounds.

The reducing carbohydrate may be added as an aqueous solution. The mixture may then be pre-heated with conventional heated mixing equipment before cooking at higher temperature under reduced pressure.

A nutritional supplement for use in ruminant feed comprises rumen-protected one or more lipid-soluble nutritional supplement compounds prepared by the above-described method. The reducing carbohydrate can range from about 1% to about 49%, or about 2% to about 40%, or about 3% to about 30% based on the weight of the final supplement formula.

For the supplement, the rumen-protected nutritional supplement can be a liquid product dried onto a matrix. The matrix can be selected from the group consisting of soybean meal, corn meal, silicates, rice hulls, mill run, ground corn, dried corn gluten feed, citrus pulp, oats hulls, sorghum grain, wheat mill run, sunflower meal, wet distiller's grains, dry distillers' grains aluminum silicates, diatomaceous earths, maltodextrins, maltodextrose, wheat midds, and mixtures of two or more thereof.

A method for modulating the fatty acids profile of milk or meat within the normal reference range for ruminants, comprises feeding an effective amount of the above-described PUFA supplement to the ruminant. The supplement can be fed daily, at a total dose of 1 g to 50 g daily, but will depend on the metabolic weight of the animal. See Table 1 below.

TABLE 1

| Metabolic weight and dose | | |
|---|---|---|
| Ruminant animal | Weight, Kg | Dose Range, g/day |
| Sheep | 20 | 2-3 |
| Early weaned Calf | 80 | 8-9 |
| Calf | 160 | 11-15 |
| Calf | 200 | 13-18 |
| Yearling | 350 | 20-28 |
| Beef cow | 500 | 26-36 |
| Small frame dairy cow | 650 | 32-44 |
| Big frame dairy cow | 750 | 35-49 |
| Bull | 1000 | 44-61 |

A method for treating or preventing stress and downregulating inflammation in ruminant animals, comprises feeding an effective amount of the above-described PUFA supplement to the ruminant animals. The ruminant animals can be selected from dairy cows, beef cows, finishing steers, growing steers, pregnant ewes, finishing lambs, calves and early weaned calves.

A method of providing lipid-soluble nutritional supplement compounds to the diet of a ruminant animal is provided by feeding an effective amount of the nutritional supplement to the ruminant animals. The ruminant animals can be selected from dairy cows, beef cows, finishing steers, growing steers, pregnant ewes, finishing lambs, calves and early weaned calves.

A method for enhancing the pregnancy rate in cows or ewes, comprises feeding an effective amount of the above-described PUFA supplement containing other lipid-soluble nutraceuticals to the ruminants. The ruminant animals can be selected from dairy cows, beef cows, and ewes. A related method for treating cows experiencing fertility problems, comprises feeding an effective amount of the above-described supplement to such cows. The cows can be selected from dairy cows and beef cows.

A method for treating or preventing stress in ruminant animals in transition, comprises feeding an effective amount of the above-described supplement containing PUFAs and one or more lipid-soluble nutraceuticals to the ruminant animals, from before calving up to end of lactation. The ruminant animals in transition can be selected from dairy cows or beef cows. The supplement can be fed from about 21 days before calving up to about 21 days post calving.

A method of influencing the productive performance of the offspring, known as fetal programming, comprises feeding the above PUFA supplement to ruminant animals during the last trimester of gestation.

A method of modulating the expression of lipogenic genes in ruminant offspring comprises feeding an effective amount of the above PUFA supplement containing other lipid-soluble nutraceuticals to the ruminant mother. The lipogenic genes having enhanced expression can include those genes controlling fatty acid synthase and diacylglycerol acyltransferase. Stated alternatively, the method of modulating gene expression in ruminant offspring comprises feeding an effective amount of the above PUFA supplement to the dam, where the genes are selected from the group consisting of genes of hormone sensitive lipases and hormone receptors. Enhanced gene expression will enhance the performance of the offspring. See, for Example, Danielle N Coleman, Ana C Carranza Martin, Yukun Jin, Kichoon Lee, Alejandro E Relling, Prepartum fatty acid supplementation in sheep. IV. Effect of calcium salts with eicosapentaenoic acid and docosahexaenoic acid in the maternal and finishing diet on lamb liver and adipose tissue during the lamb finishing period, *Journal of Animal Science*, Volume 97, Issue 7, July 2019, Pages 3071-3088; and Ana Cristina Carranza Martin, Danielle Nicole Coleman, Lyda Guadalupe Garcia, Cecilia C Furnus, Alejandro E Relling, Prepartum fatty acid supplementation in sheep. III. Effect of eicosapentaenoic acid and docosahexaenoic acid during finishing on performance, hypothalamus gene expression, and muscle fatty acids composition in lambs, *Journal of Animal Science*, Volume 96, Issue 12, December 2018, Pages 5300-5310.

The foregoing and other aspects of the present invention will be better appreciated by reference to the following drawing and detailed description set forth below.

DETAILED DESCRIPTION

Figure 1:
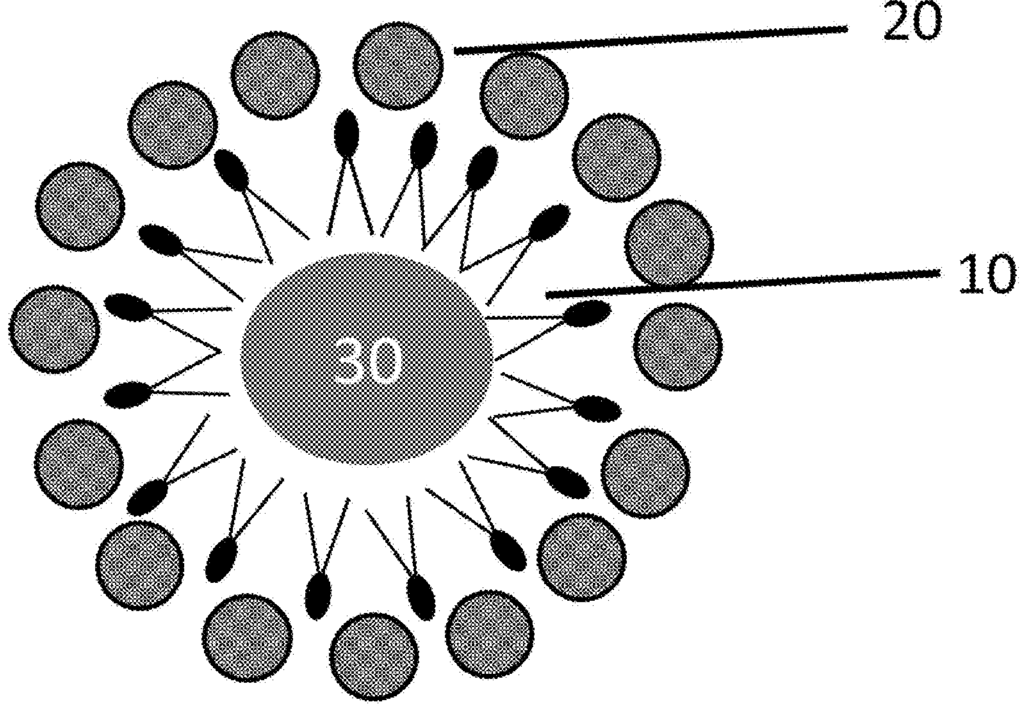
FIG. 1 shows a schematic structure drawing of a typical rumen-protected PUFA (RuPUFA) prepared according to the disclosed process. 10 is lecithin, 20 is reducing sugar, and 30 is PUFA.

A body of scientific evidence now suggests that the milk or meat endproducts of ruminant animals, including the fatty acid composition of the milk or meat can be manipulated by the polyunsaturated fatty acids fed in the diet. It is also known that DHA is a potent antiinflammatory when fed to cows under stressful conditions, aiding the immune system to cope with stress, and assisting with pregnancy. It can also help maintain the integrity of the intestinal barrier and its function.

For purposes of the present invention, "stress" is defined according to the definition of livestock stress employed by animal physiologists, in which "stress" consists of external body forces that tend to displace homeostasis and "strain" is the internal displacement brought about by stress, wherein there are environmental forces continuously acting upon animals that disrupt homeostasis.

As disclosed herein, a number of ranges of values are provided. It is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention. The term "about" generally includes up to plus or minus 10% of the indicated number. For example, "about 10%" may indicate a range of 9% to 11%, and "about 20" may mean from 18 to 22. Preferably "about" includes up to plus or minus 6% of the indicated value. Alternatively, "about" includes up to plus or minus 5% of the indicated value. Other meanings of "about" may be apparent from the context, such as rounding off, for example, "about 1" may also mean from 0.5 to 1.4.

The supplement components of the present invention can be in the form of dry fine powders, or liquids. The energy supplement can be made by weighing and mixing together the component quantities with up to 25% by weight of distilled water, in any equipment suitable for mixing materials. The reducing sugar is dissolved in heated water first and then mixed with a blend of lipid-soluble materials and lecithin. The mixture is then heated under reduced pressure to between about 60 and about 95° C., preferably between about 60 and about 90° C., more preferably at about 85° C., at a pressure between about 0.4 and less than 1.0 Atm, preferably at about 0.85 Atm for about 7 minutes to about 2 hours, preferably between about 30 and about 45 minutes, and then cooled to room temperature. Table 2, below, indicates the appropriate temperatures and pressures determined to be useful for the reduced pressure Maillard reaction for the formation of a rumen-protected PUFA:

TABLE 2

Reaction conditions for Maillard synthesis of rumen-protected PUFA (RuPUFA)

| Temperature (° C.) | Pressure (ATM) |
|---|---|
| 100 | 1 |
| 95 | 0.83 |
| 90 | 0.70 |
| 85 | 0.59 |

TABLE 2-continued

| Reaction conditions for Maillard synthesis of rumen-protected PUFA (RuPUFA) | |
|---|---|
| Temperature (° C.) | Pressure (ATM) |
| 80 | 0.51 |
| 75 | 0.46 |
| 70 | 0.44 |
| 65 | 0.44 |
| 60 | 0.44 |

A typical rumen-protected PUFA formulation is depicted in Table 3, together with the acceptable ranges within which individual components can be varied:

TABLE 3

| Ranges of components in the RuPUFA | | | |
|---|---|---|---|
| | International | Proportion (g/kg) | |
| Ingredient | Feed Number | Preferred[1] | Range |
| 1. DHA | | 350 | 10-800 |
| 2. Lecithin | | 620 | 300-800 |
| 3. Dextrose | 6-02-633 | 30 | 1-300 |

[1]Preferred for the specific PUFA, DHA

The supplement of the present invention can also be optionally formulated with alternative carbohydrate sources (other than dextrose) in accordance with availability and pricing of ingredients. Fructose, sucrose treated to yield glucose and fructose, high fructose corn syrup, glucose, lactose, molasses, xylose, and spent sulfite liquor, as well as other reducing sugars can be used as the optional carbohydrate source.

The supplement can also be formulated with a bulk source of DHA, such as fish oil, marine algae products, or any other bulk source of DHA.

The supplement can also be formulated with one or more of lipid-soluble nutrients, such as nutraceuticals, essential oils or lipid-soluble medicaments instead of PUFAs, or in admixture with PUFAs.

The term "lipid-soluble medicament" includes "lipid-soluble nutraceuticals" and "lipid-soluble pharmaceuticals", where the lipid-soluble compounds have a log P (logarithm of the partition coefficient between n-octanol and water; also known as log $K_{OW}$) of 1 or higher, preferably 2 or higher, and particularly 3 or higher. Lipinski's Rule of 5, an empirical drug discovery rule developed at Pfizer in the 1990s, states that the log P of a compound intended for oral administration should be less than 5.

Lipid-soluble nutraceuticals include, but are not limited to, essential oils, such as basil oil, carrot seed oil, celery seed oil, Citronella oil, coriander oil, garlic oil, grapefruit oil, lemon oil, marjoram oil, onion oil, organum oil, parsley oil, rosemary oil, sage oil, tarragon oil, thyme oil, cannabis oil, and any other lipid-soluble plant extract. Two or more of these can also be combined.

The lecithin can be from soybean, sunflower, rape seed, or any other available lecithin source. The lecithin should be de-oiled by extraction with a solvent, such as acetone, hexane, and related solvents, to remove the residual oil and sterols before mixing with the DHA or other PUFA source. Optionally, the de-oiled lecithin can be further extracted with an alcohol, such as methanol, to remove residual sugars. In preferred embodiments the de-oiled lecithin is extracted with alcohol (e.g., methanol) to remove residual sugars.

When the supplement is prepared in a liquid medium, to produce a liquid product, the resulting liquid product can be applied to and dried onto various matrices, such as soybean meal, corn meal, silicates (verixite, vermiculite, etc.), rice hulls, mill run, ground corn, citrus pulp, oats hulls, sorghum grain, wheat mill run, aluminum silicates, diatomaceous earths, maltodextrins, maltodextrose, dry distillers grains, wet distillers grains, wheat midds, or a blend of two or more of these.

The supplement of the present invention can be conveniently fed to a ruminant admixed with a conventional ruminant feed. Feeds are typically vegetable materials edible by ruminants, such as grass silage, corn silage, legume silage, legume hay, grass hay, corn grain, oats, barley, distiller's grain, brewer's grain, soya bean meal, and cottonseed meal. Concentrates or grains are preferred. Concentrates are mixtures of cereals and minerals that are typically pelleted and fed to the animals. A representative example of a concentrate is 55% corn, 20% wheat bran, 20% soybean meal and 5% mineral mixture.

For ruminant animals weighing over 500 kg (e.g., young or adult cows), between about 10 and about 100 grams per day of the supplement should be administered, preferably between about 5 and about 60 grams, and more preferably about 55 grams per day. For ruminant animals weighing between about 80 kg and about 300 kg (e.g., young or adult sheep), between about 14 and about 60 grams should be administered, preferably about 25 grams per day. For ruminant animals weighing under 150 kg (e.g., young or adult goats), between about 10 and about 40 grams should be administered, preferably about 20 grams per day.

The nutritional compositions are intended to be fed to ruminant animals on a daily basis. Ruminants to which the compositions of the present invention can be fed include cattle, goats, sheep, and any other ruminant animal. The period for administration to ruminant animals should be from about one to three months before calving up to the end of lactation. The preferred administration period for ruminant will depend on the physiological parameter that is to be changed. In dairy cows weighing over 500 kg is about one month before calving up to the end of lactation, and more preferably about 20 days before calving to about 30 days after calving. The preferred administration period for ruminant animals weighing between about 80 kg and about 300 kg is about 50 days before calving to the end of lactation, more preferably for about 14 days before calving until about 28 days afterwards. The preferred administration period for ruminant animals weighing under 150 kg is about 14 days before parturition up to the end of lactation, more preferably about 14 days before calving until about 21 days afterwards.

One aspect of the invention is directed to a method of preparing one or more essential oils protected from ruminal degradation, the method comprising:

mixing de-oiled lecithin with a source of one or more essential oils, heating and then adding an aqueous reducing carbohydrate solution to the mixture, where the amount by weight of the reducing carbohydrate source versus the amount by weight of the lecithin ranges from about 10:90 to less than 50:50, to provide a mixture; and heating the mixture for a sufficient amount of time, at a sufficient temperature and under reduced pressure, in the presence of sufficient moisture so that a Maillard reaction product is formed, where the amount of lecithin and the heating time, temperature, reduced pressure and moisture conditions are sufficient to provide an amount of a Maillard reaction product effective to prevent ruminal degradation of the one or more essential oils.

The reaction can be performed on neat lipid-soluble essential oils, or lipid-soluble essential oils may be in admixture with one or more PUFAs, such as DHA. For purposes of the present invention the admixture is defined as a PUFA supplement containing lipid-soluble essential oils.

The weight percent of the reducing carbohydrate source versus the lecithin is about 5:95, or about 7:93, or about 10:90, or about 20:80, or about 30:70, or about 40:60, or less than 50:50. The weight ratio of reducing carbohydrate to lecithin can be about 5:95. The weight ratio of reducing carbohydrate to lecithin can be about 7:93. The weight ratio of reducing carbohydrate to lecithin can be about 10:90. The weight ratio of reducing carbohydrate to lecithin can be about 30:70. The weight ratio of reducing carbohydrate to lecithin can be about 40:60. The weight ratio of reducing carbohydrate to lecithin can be less than 50:50.

The lecithin provides reactive nitrogen groups for formation of the Maillard reaction product.

The reducing carbohydrate source can be selected from the group consisting of fructose, sucrose which has been treated to yield glucose and fructose, dextrose, high fructose corn syrup, glucose, lactose, molasses, xylose, spent sulfite liquor, and mixtures of two or more thereof. The reducing carbohydrate source can comprise sucrose treated to yield glucose and fructose, glucose, dextrose, fructose or mixtures of two or more thereof. The reducing carbohydrate source can be dextrose. The reducing carbohydrate source can be sucrose treated to yield glucose and fructose. The reducing carbohydrate source can be glucose. The reducing carbohydrate source can be fructose and/or high fructose corn syrup, or any other reducing carbohydrate.

The mixture is heated to a temperature between about 30° C. and about 135° C. The mixture can be heated to a temperature between about 30° C. and about 95° C., or between about 60° C. and about 90° C., or between about 60° C. and about 85° C., or between about 60° C. and about 80° C. The mixture can be heated to a temperature between about 40° C. and about 95° C., or about 45° C. and about 90° C., or about 50° C. and about 85° C., or about 55° C. and about 80° C., or about 60° C. and about 75° C. The pressure during heating can be between about 0.4 Atm and about 0.9 Atm, or about 0.4 Atm and about 0.8 Atm, or between about 0.4 Atm and about 0.9 Atm, or between about 0.4 Atm and about 0.6 Atm, or between about 0.4 Atm and about 0.5 Atm. The pressure during heating can be about 0.4 Atm, or about 0.45 Atm, or about 0.5 Atm, or about 0.55 Atm, or about 0.6 Atm, or about 0.65 Atm, or about 0.7 Atm, or about 0.75 Atm, or about 0.8 Atm, or about 0.85 Atm, or about 0.9 Atm, or about 0.95 Atm.

The mixture heating time can be about 7 min to about 120 min. The mixture heating time can be about 7 min or about 10 min, or about 15 min, or about 20 min, or about 25 min, or about 30 min, or about 35 min, or about 40 min, or about 45 min, or about 50 min, or about 55 min, or about 60 min, or about 65 min, or about 70 min, or about 75 min, or about 80 min, or about 85 min, or about 90 min, or about 95 min, or about 100 min, or about 105 min, or about 110 min, or about 115 min, or about 120 min. Alternatively, the mixture heating time can be up to about 240 min, such as about 7 min to about 240 min, or about 150 min, or about 175 min, or about 200 min, or about 225 min, or about 240 min.

The method of preparing a PUFA protected from ruminal degradation can comprise: mixing a reducing carbohydrate source and de-oiled lecithin together with a lipid soluble fraction containing one or more PUFAs to be protected and one or more lipid-soluble nutraceutical compounds, to provide a mixture; and heating the mixture for about 7 min to about 120 min (alternatively, up to about 240 min), at a temperature between about 30° C. and about 135° C., and a pressure between about 0.4 Atm and about 0.9 Atm, in the presence of sufficient moisture so that a Maillard reaction product is formed in an amount sufficient to prevent ruminal degradation of the PUFA.

Lipid-soluble nutritional supplements, for example, one or more of the above-listed nutraceuticals, such as essential oils, can be added to the mixture prior to the heating step. A PUFA supplement for use in ruminant feed comprises rumen-protected PUFA (RuPUFA) prepared by any of the above-described methods. The RuPUFA can range from about 10% to about 90%, or about 15% to about 85%, or about 15% to about 80%, or about 20% to about 75%, or about 20% to about 70%, in the final supplement formula.

The PUFA supplement mixing step can optionally further comprise a pH adjustment agent. The pH adjustment agent can comprise a buffer. The buffer components can be selected from one or more of sodium bicarbonate, potassium dihydrogen phosphate, dipotassium hydrogen phosphate, sodium hydroxide or phosphoric acid. The buffer can consist essentially of about 50% sodium bicarbonate, about 20% potassium dihydrogen phosphate, and about 30% dipotassium hydrogen phosphate, or about 10% sodium hydroxide.

Optionally, the pH of the PUFA supplement can be adjusted to about 2 to about 11, about 3 to about 10, about 4 to about 9, about 5 to about 8.5, about 6 to about 8.5, or about 6 to about 8. The pH can be about 2, about 2.5, about 3, about 3.5, about 4, about 4.5, about 5, about 5.5, about 6, about 6.5, about 7, about 7.5, about 8, about 8.5, about 9, about 9.5, or about 10, about 10.5, or about 11.

For the lipid-soluble nutritional supplement, the rumen-protected product can be a liquid product dried onto a matrix. The matrix can be selected from the group consisting of soybean meal, corn meal, silicates, rice hulls, mill run, ground corn, citrus pulp, oats hulls, sorghum grain, maltodextrose, maltodextrins, aluminum silicates, diatomaceous earths, wheat mill run, wheat midds, and mixtures of any two or more thereof.

A method for treating stress in ruminant animals in transition comprises feeding an effective amount of the above-described PUFA supplement, with or without other lipid-soluble nutritional supplements, to the ruminant animals, from before calving up to end of lactation. The ruminant animals in transition can be selected from dairy cows or beef cows. The PUFA supplement can be fed from about 21 days before calving up to about 21 days post calving.

A method for treating cows experiencing fertility problems, comprises feeding an effective amount of the above-described PUFA supplement to such cows, with or without other lipid soluble nutritional supplements. The cows can be selected from dairy cows and beef cows.

EXAMPLES

Example 1. Purification of Lecithin (De-Oiled Lecithin)

The typical ranges of soybean lecithin components are as follows:

TABLE 4

Typical ranges of soybean lecithin components

| Component | Weight % |
|---|---|
| Phosphatidylcholine | 19-21 |
| Phosphatidylethanolamine | 8-20 |
| Inositol Phosphatides | 20-21 |
| Other Phosphatides | 5-11 |
| Soybean Oil | 33-35 |
| Sterols | 2-5 |
| Free Carbohydrates | ca. 5 |
| Water | ca. 1 |

Soybean lecithin is purified by de-oiling using solvent extraction, which removes residual soybean oil and sterols. The lecithin is mixed with a suitable solvent, typically acetone or hexane, typically in a weight ratio of about 1:1 lecithin:solvent. After a suitable mixing time, the solid is separated from the liquid phase. The solid lecithin residue is recovered in about 65% yield after drying, based on the original lecithin. The de-oiled lecithin residue can be further purified to remove carbohydrates by extracting with an alcohol, such as methanol.

Lecithin obtained from an extrusion and press process was mixed with acetone in a proportion of 100 g of lecithin and 30 g of acetone and mixed for 5 minutes. This suspension was centrifuged for 90 minutes at 300 RPM. The suspension separated into two phases, the supernatant, that is the acetone plus the residual oil, was discarded, and the solid part used in the mixtures prepared for the experiments.

Example 2. Typical Preparation of a Rumen-Protected PUFA (RuPUFA)

The purified lecithin of Example 1 was mixed according to Table 5 with a PUFA source, typically fish oil or algae, typically in a weight ratio of about 65:35 purified lecithin: PUFA source. The mixture was heated to about 30° C. and the reducing carbohydrate was added together with enough water to give a moisture content of about 20% to 25% by weight. Heating was continued at about 85° C. for about 2 hours under a vacuum of 0.85 Atm until the water has evaporated, providing the rumen-protected PUFA.

TABLE 5

Typical ranges of components for rumen-protected DHA (RuDHA)

| Ingredient | International Feed Number | Proportion (g/kg) Preferred[1] | Range |
|---|---|---|---|
| 1. Fish Oil (20% DHA) | | 350 | 10-800 |
| 2. Lecithin | | 550 | 300-800 |
| 3. Dextrose | 6-02-633 | 100 | 1-300 |

The rumen-protected PUFA, is optionally mixed with a carrier, such as bentonite.

Example 3. Selection of Parameters

The objective of this experiment was to select a heating time and a mixture of modified lecithin, sugar, and fish oil that would have the lowest biohydrogenation when tested using an in vitro fermentation technique.

Maillard Reaction Sample Preparation

De-oiled lecithin was obtained as described above. De-oiled lecithin was mixed with fish oil until a paste was obtained; dextrose was added to hot water (60° C.) and mixed until it was dissolved. The aqueous sugar solution was added to the de-oiled lecithin/fish oil mixture, and vortex-mixed for 10 minutes.

Four different products were prepared:

3A) 24% Fish oil 52% modified lecithin, 4% sugar and 20% water;

3B) 24% Fish oil 48% modified lecithin, 8% sugar and 20% water;

3C) 32% Fish oil 44% modified lecithin, 4% sugar and 20% water; and 3D) 32% Fish oil 40% modified lecithin, 8% sugar and 20% water (see Table 6). Samples were heated for 3 or 6 hs in a vacuum oven at 85° C. and 0.85 ATM.

TABLE 6

Maillard reaction samples 3A-3D

| Sample | Fish oil (%) | Lecithin (%) | Sugar (%) | Water (%) | Total (g) |
|---|---|---|---|---|---|
| 3[a] | 24 | 52 | 4 | 20 | 100 |
| 3B | 24 | 48 | 8 | 20 | 100 |
| 3C | 32 | 44 | 4 | 20 | 100 |
| 3D | 32 | 40 | 8 | 20 | 100 |

Example 4. In Vitro Test

Heated samples and unheated controls of each mixture were incubated in vitro according to Goering and Van Soest 1970 modified Technique (Goering, H. K. and Van Soest, P. J. (1970) Forage fiber analyses (apparatus, reagents, procedures, and some applications); No. 379. US Agricultural Research Service).

In 50 mL test tubes, 0.5 g of substrate (alfalfa hay and corn grain 50:50 V:V) and 30 mg of samples 3A to 3D (3 replicates per sample).

Once the substrate and the samples were in the tubes, 30 mL of fresh rumen liquid was added under 02-free conditions.

The tubes were capped and incubated for 4, 8, and 12 hours.

A sample without incubation was separated and used as the 0 hour incubation control. At the end of each incubation time, tubes were flash frozen in liquid nitrogen to stop all biohydrogenation.

Once all the samples were collected, fatty acids were extracted and methylated using the procedure described by Folch et al. (Folch, J., Lees, M., and Stanley, G. H. S. (1957) A simple method for the isolation and purification of total lipids from animal tissues. The Journal of Biological Chemistry, 226: 497-509) and analyzed using a gas chromatography as described by Coleman et al. (Coleman, D. N., Rivera-Acevedo, K. C., and Relling A. E. (2018) Prepartum fatty acid supplementation in sheep I. Eicosapentaenoic and docosahexaenoic acid supplementation do not modify ewe and lamb metabolic status and performance through weaning. J Anim Sci. 96:364-374).

Data was analyzed as a biohydrogenation protection (%) using the fatty acid concentration of the time 0 as a 100% of the fatty acid. Statistical analysis was evaluated using a mixed model that include the treatments as fixed variables and the replications as random.

Results

Biohydrogenation of DHA and EPA

Figure 2:
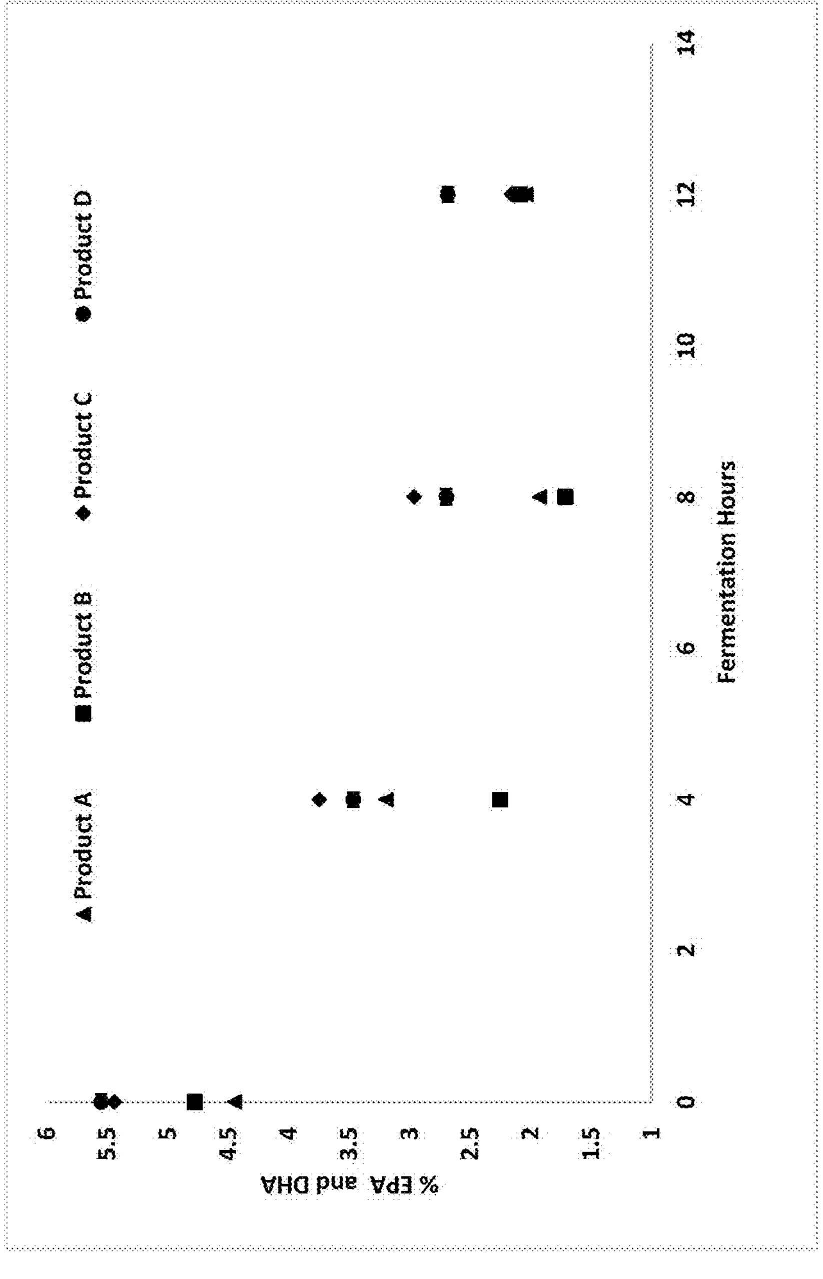
FIG. 2 is a graph showing the in vitro biohydrogenation of DHA %±EPA % at incubation times of 4, 8 and 12 hours.
Figure 3:
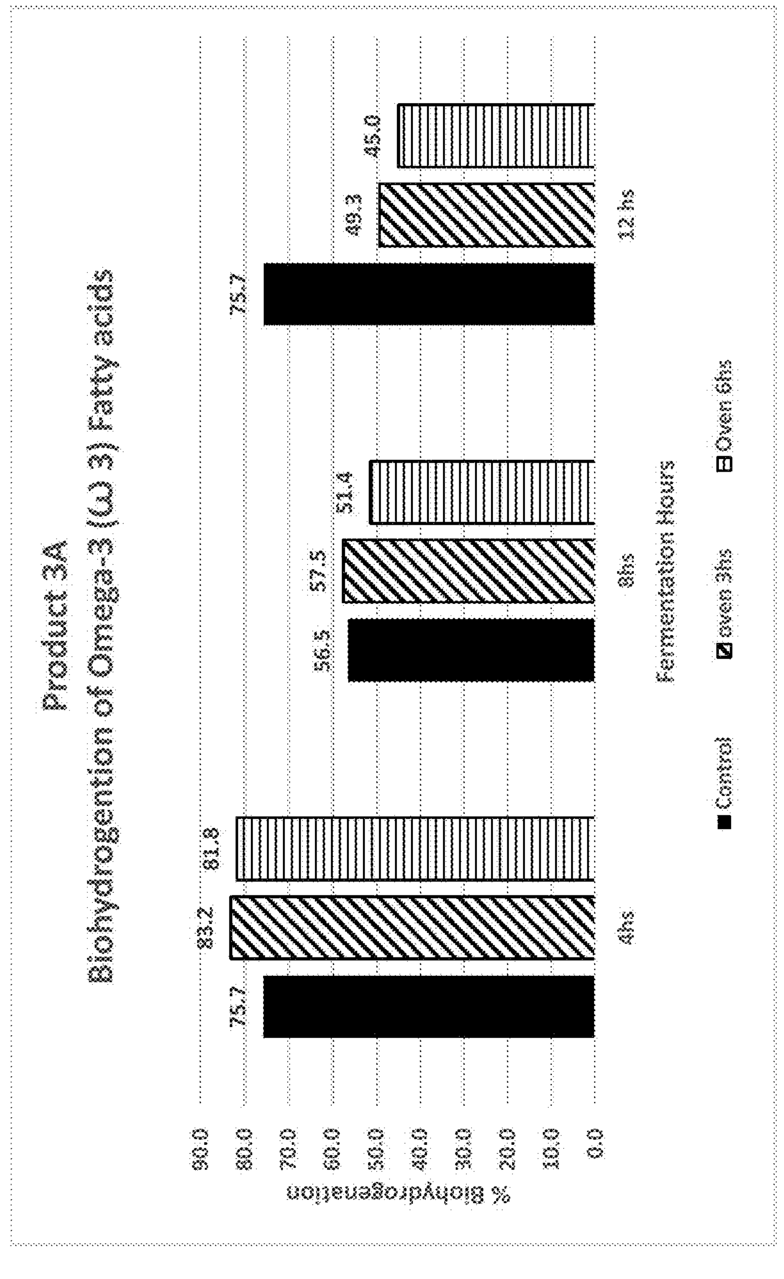
FIG. 3 is a graph showing Product 3A % of Biohydrogenation of Omega-3 (03) fatty acids according to in vitro fermentation hours 4, 8 or 12 and heating time control (unheated), 3 hs heating or 6 hs heating.
Figure 4:
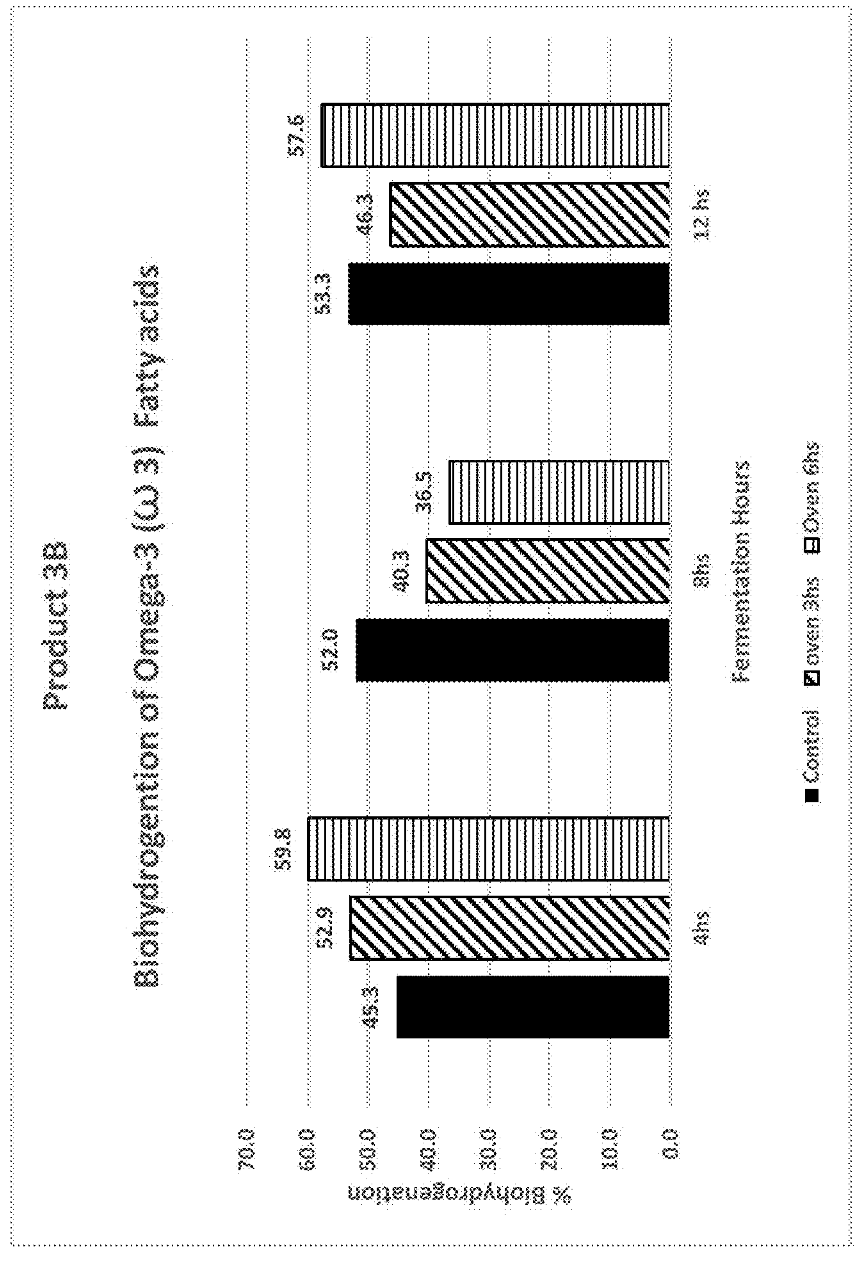
FIG. 4 is a graph showing Product 3B % of Biohydrogenation of Omega-3 (03) fatty acids according to in vitro fermentation hours 4, 8 or 12 and heating time control (unheated), 3 hs heating or 6 hs heating.
Figure 5:
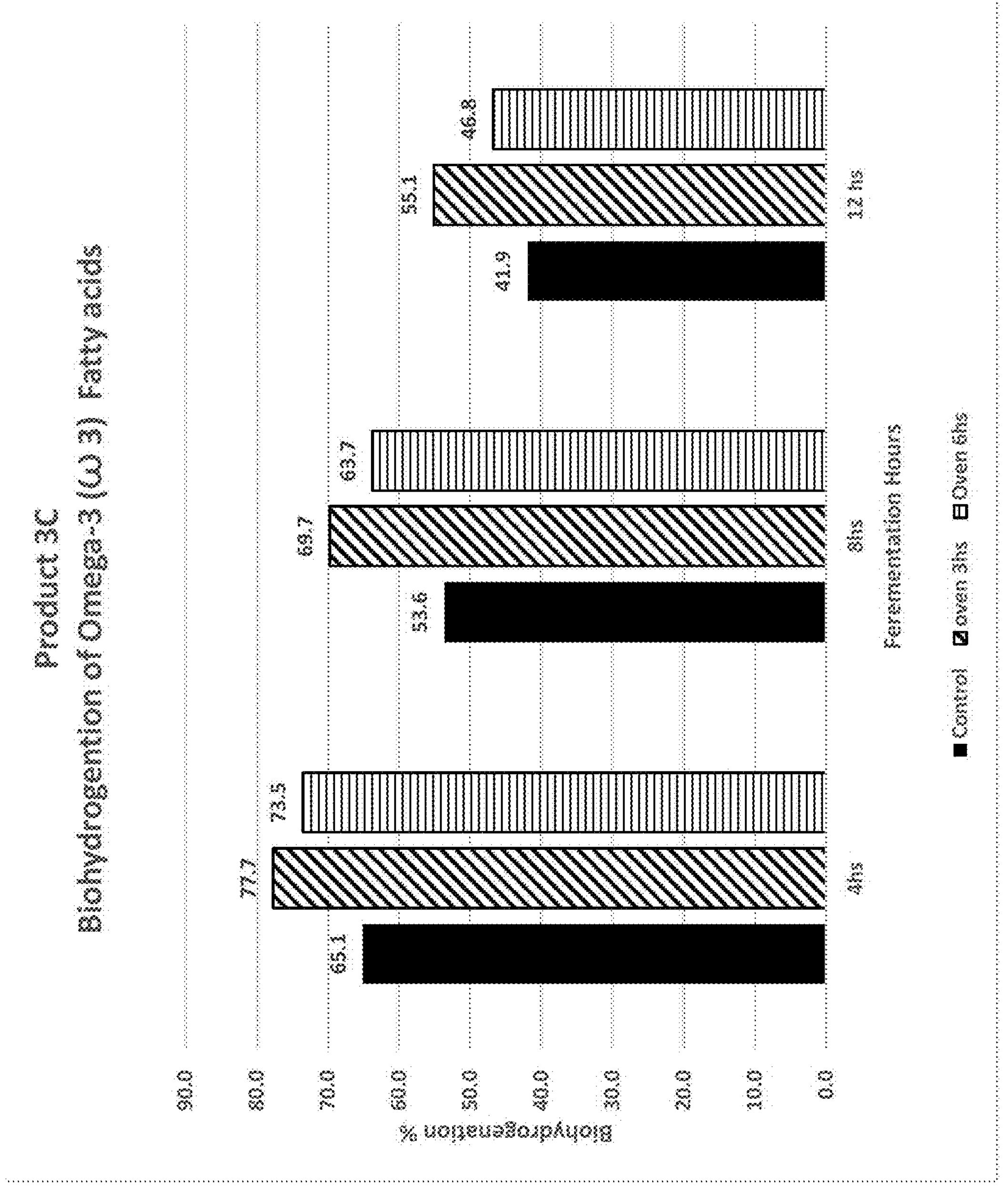
FIG. 5 is a graph showing Product 3C % of Biohydrogenation of Omega-3 (03) fatty acids according to in vitro fermentation hours 4, 8 or 12 and heating time control (unheated), 3 hs heating or 6 hs heating.
Figure 6:
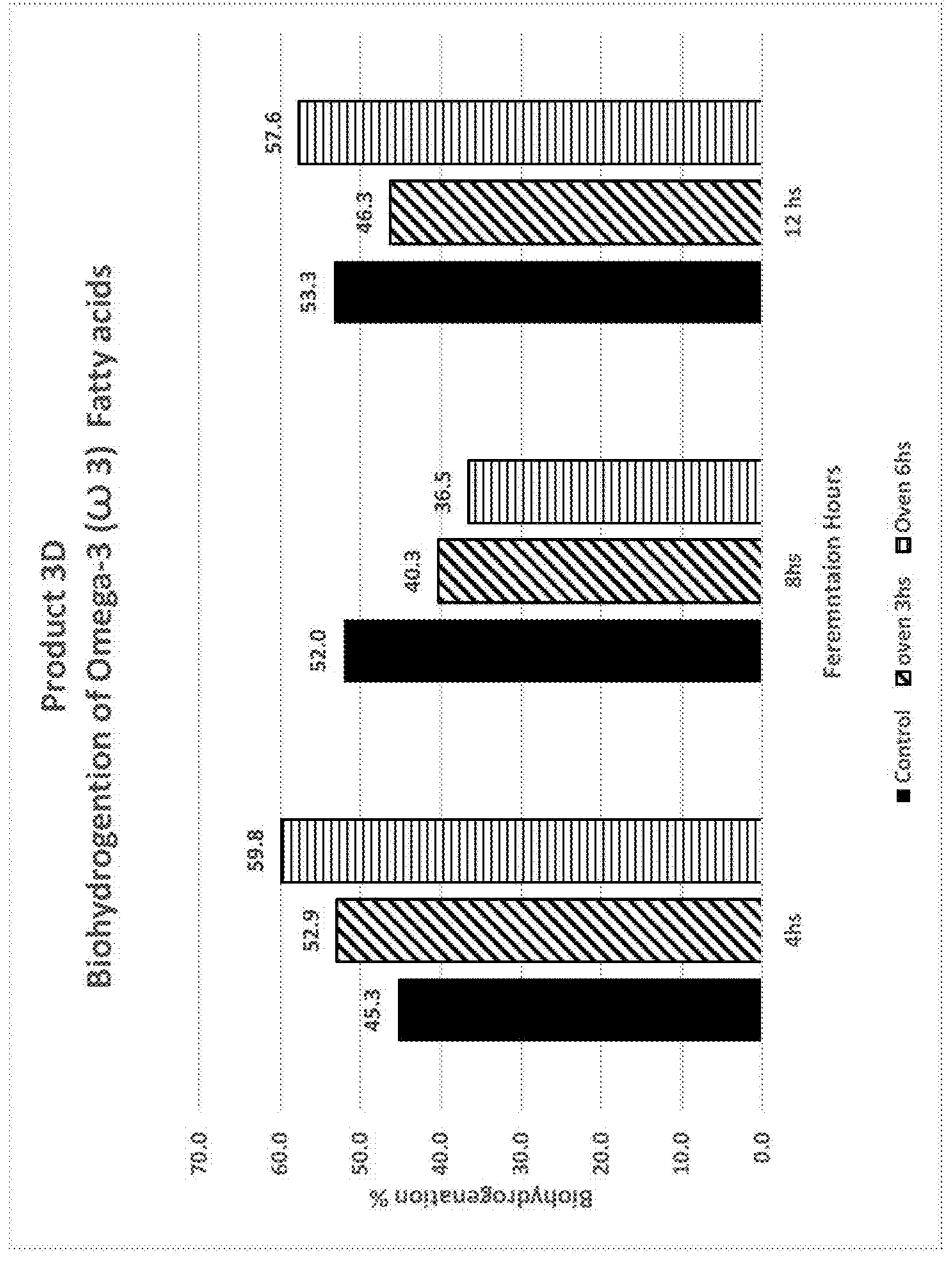
FIG. 6 is a graph showing Product 3D % of Biohydrogenation of Omega-3 (03) fatty acids according to in vitro fermentation hours 4, 8 or 12 and heating time control (unheated), 3 hs heating or 6 hs heating.

In vitro biohydrogenation of Docosahexaenoic fatty acid % (DHA %) plus ecosapentanoic fatty acid % (EPA %) was reported versus the hours of incubation. Products 3A and 3C showed the lowest biohydrogenation regardless of the heating time in the oven (FIG. 2).

Biohydrogenation of Omega-3 (ω3) Fatty Acids

Total Omega-3 (ω3) fatty acids of each product were analysed to evaluate the preferred heating time to yield the lower biohydrogenation (FIGS. 3, 4, 5 and 6 for products 3A, 3B, 3C, and 3D Respectively). Product 3C was the product that had the lowest biohydrogenation at 3 hs heating time, for an 8 hs in vitro fermentation.

Example 5. Digestibility Determination of Prototype Feeds

The objective of this experiment was to measure the digestibility of two prototype feeds of rumen-protected lipids enriched with ω-3. The prototype feeds were selected from the previous in vitro fermentation experiment, and the digestibility was measured using cockerels.

Materials and Methods

Birds: Twenty-four Leghorn cockerels were used (hy-line W-80) from Cabaña Avicola Feller, Argentina. Cockerels were 85 weeks old and weighed 2.5 kg. The animals were housed in individual cages.

Experimental Design.

The experimental design was a completely randomized design with 4 treatments and 6 repetitions (1 cock per repetition).

Diets and Treatments: Lecithin was de-oiled as above. Maillard reaction samples were prepared as described in Example 3.

The protected lipids were selected from the four mixes tested in the previous fermentation trial, Samples 3A-3D. This was expanded to include the mix described in Table 7, below. This latter product was also heated at two different times (3 and 6 hours) at 85° C. and 0.85 ATM.

TABLE 7

| Protected oil mix | |
|---|---|
| Protected oil mix | % |
| Fish oil | 40 |
| Treated Lecithin | 55 |
| Sugar dextrose | 5 |
| Water | 20 g of water per 100 gr of product |

The technique used to feed the cockerels was the fillers replacement technique adapted from Adeola (Adeola O. 2001. Digestion and balance techniques in pigs. In AJ Lewis & LL Southern, eds. Swine Nutrition. 2nd ed. Washington, DC, USA: CRC Press LLC. Ch. 40. pp. 903-916). This methodology feeds rations with 80% corn and fills the rest of the diet with the materials to be tested, it also adds one treatment with crystalline cellulose (which is not digestible by the bird) to control for the lipids presented in the basal diet (corn) and its digestibility. Therefore, the 4 treatments were 1) 80% corn and 20% crystalline cellulose, 2) 80% corn and 20% unheated product, 3) 80% corn and 20% product heated for 3 hours, and 4) 80% corn and 20% product heated for 6 hours (Table 8).

TABLE 8

| Diets fed to cockerels | | | | | |
|---|---|---|---|---|---|
| Treatments | Corn | Celulose* | Control (unheated) | Product 3 hs | Product 6 hs |
| Corn + Celulose | 80% | 20% | | | |
| Control, no heat | 80% | | 20% | | |
| heated 3 hs | 80% | | | 20% | |
| heated 6 hs | 80% | | | | 20% |

*Microcrystalline cellulose, used as inert material

Moisture content was determined for the three products evaluated and for the 4 diets according to the standard method (AACC. 2009. Method 44-16.01. Moisture-air-oven (aluminum-plate) method. In Approved Methods of Analysis. 1 lth ed. St. Paul, MN, USA: AACC International. Approved 1995).

Lipid Content

Total lipid content of the diets and products was determined using a Twisselman extractor according to the standard method (AACC. 2009. Method 30-25.01. Crude fat in wheat, corn, and soy flour, feeds, and mixed feeds. In Approved Methods of Analysis. 1 lth ed. St. Paul, MN, USA: AACC International. Approved 1995).

Lipids Digestibility

The 24 cockerels housed in individual cages were fasted for 24 h to ensure that the digestive tract was empty. After this period the cockerels were tube-fed 40 g of the diet to be analyzed, all the diets were around to pass through a sieve of 4.76 mm. Excreta from the cockerels were collected by 48 hs after feeding and were dried in an oven at 60° C. for 48-72 h.

Dried excreta samples and diets were analyzed for total lipids content with a Twisselman extractor following the methodology described by the AACC (2009, reference above). Knowing the total lipids in the feed and the in the excreta, digestibility of lipids was calculated with the following equation:

$$LipDigTrt = [LIPcTrt - LIPcMz) - (LIPexcTrt - LIPexcMZ)] / (LIPcTrt - LIPcMz) * 100$$

where

LipDigTrt: Digestible lipids (%)

LIPc: Intake of Lipids (g)

LIPexc: Excreted lipids (g)

Trt: Treatment (control or heated in the oven)

Statistical Analysis

Data was analyzed as complete randomized block design using linear mixed model. When p values were less than 0.05 the comparison among means was done using Tukey Test.

The software used was InfoSTAT (Di Rienzo J A, Casanoves F, Balzarini M G, Gonzalez L, Tablada M & Robledo C W. 2012. [software estadístico]. InfoStat. Cordoba, Argentina) integrated with R (R Core Team. 2017. A language and environment for statistical computing. http://www.R-ptojectorg/. Vienna, Austria) to run the mixed linear models.

Results

The digestibility of lipids of evaluated products was significantly different compared with the treatment of corn±cellulose (P<0.0001) (Table 9). There were no significant differ-ences between the control and either the 3 hrs heated product or the 6 hs heated product (P>0.05).

TABLE 9

Digestibility of lipids

| | Mz + Cel | Control | Trt 3hs | Trt 6hs | SEM | P-Value |
|---|---|---|---|---|---|---|
| Dig lipids % | $87.62^{a}$ | $96.76^{b}$ | $95.54^{b}$ | $96.43^{b}$ | 0.34 | <0.0001 |

$^{a, b}$variables with different superscript P-value < 0.01

In conclusion, based on Example 4, we observe that the lipids are efficiently protected from ruminal degradation in vitro, and based on Example 5, that these rumen-protected lipids can be absorbed efficiently in vivo by cockerels.

What is claimed is:

1. A method of preparing a lipid-soluble nutritional supplement protected from ruminal degradation comprising:

mixing a reducing carbohydrate source and de-oiled lecithin with a lipid-soluble fraction comprising one or more lipid soluble nutritional supplements, wherein the amount by weight of the reducing carbohydrate source is less than the amount by weight of the de-oiled lecithin and is less than the weight of the lipid-soluble fraction, to provide a mixture; and heating the mixture for about 7 min to about 240 min, at a temperature between about 30° C. and about 135° C., and pressure between about 0.4 atm and about 0.9 atm, in the presence of sufficient moisture so that a Maillard reaction product is formed, wherein the amount of de-oiled lecithin and the heating time, temperature, reduced pressure and moisture conditions are sufficient to provide an amount of a Maillard reaction product effective to prevent ruminal degradation of said lipid-soluble fraction.

2. The method of claim 1 wherein said de-oiled lecithin is further extracted with an alcohol to remove residual sugars.

3. The method of claim 1, further comprising adding water to the mixture to give a moisture content of about 20% to 25% by weight.

4. The method of claim 1, where said lipid-soluble fraction comprises one or more Polyunsaturated Fatty Acids (PUFA).

5. The method of claim 4, wherein the PUFA comprises docosahexaenoic acid (DHA).

6. The method of claim 4, wherein said PUFA comprises eicosapentaenoic acid (EPA).

7. The method of claim 1, wherein the reducing carbohydrate source is selected from the group consisting of fructose, sucrose treated to yield glucose and fructose, dextrose, high fructose corn syrup, glucose, lactose, molasses, xylose, spent sulfite liquor, and mixtures of two or more thereof.

8. The method of claim 1, wherein the mixture is heated to a temperature between about 60° C. and about 85° C. at a pressure between about 0.4 atm and about 0.6 atm.

9. The method of claim 1, wherein the weight ratio of reducing carbohydrate to de-oiled lecithin is about 10:90.

10. The method of claim 1, wherein the one or more nutritional supplements comprise one or more lipid-soluble nutraceuticals.

11. The method of claim 10, wherein the one or more lipid-soluble nutraceuticals comprise one or more essential oils.

12. The method of claim 11, wherein the one or more essential oils comprise essential oils selected from the group consisting of basil oil, carrot seed oil, celery seed oil, citronella oil, coriander oil, garlic oil, grapefruit oil, lemon oil, marjoram oil, onion oil, organum oil, parsley oil, rosemary oil, sage oil, tarragon oil, thyme oil, cannabis oil, and lipid-soluble essential oil plant extract.

13. The method of claim 1, wherein the lipid-soluble fraction consists essentially of lipid-soluble nutraceutical compounds.

* * * * *